(12) United States Patent
Endo et al.

(10) Patent No.: US 6,533,725 B1
(45) Date of Patent: Mar. 18, 2003

(54) METHOD FOR EVALUATING SKIN HEALTH

(75) Inventors: Koji Endo, Tochigi; Masato Hoshi, Wakayama; Yasushi Shioya, Tokyo, all of (JP)

(73) Assignee: Kao Corporation, Tokyo (JP)

( * ) Notice: Subject to any disclaimer, the term of this patent is extended or adjusted under 35 U.S.C. 154(b) by 58 days.

(21) Appl. No.: 09/692,190

(22) Filed: Oct. 20, 2000

(30) Foreign Application Priority Data

Oct. 22, 1999 (JP) .............................. 11-301055

(51) Int. Cl.[7] ................................. A61B 5/00
(52) U.S. Cl. ......................... 600/306; 600/307
(58) Field of Search ..................... 600/306, 307, 600/587

(56) References Cited

U.S. PATENT DOCUMENTS

| | | | |
|---|---|---|---|
| 4,066,068 A | * | 1/1978 | Nilsson et al. .............. 600/307 |
| 5,131,390 A | | 7/1992 | Sakaguchi et al. |
| 5,984,868 A | * | 11/1999 | Shih et al. .................. 600/300 |
| 6,287,255 B1 | * | 9/2001 | Endo et al. .................. 600/307 |

FOREIGN PATENT DOCUMENTS

| | | | |
|---|---|---|---|
| JP | 1-238824 | 9/1989 | |
| JP | 10-286238 | * 10/1998 | ............ A61B/5/00 |

OTHER PUBLICATIONS

Derwent Publications, AN 1988–095519, JP 63 046131, Feb. 27, 1988.

* cited by examiner

*Primary Examiner*—Robert L. Nasser
*Assistant Examiner*—Patricia C. Mallari
(74) *Attorney, Agent, or Firm*—Oblon, Spivak, McClelland, Maier & Neustadt, P.C.

(57) ABSTRACT

An apparatus for evaluating water permeability of the stratum corneum epidermidis, including a feeding device for feeding a carrier gas to a skin surface to be measured, a measuring device for measuring humidity of the carrier gas discharged from the feeding device over the skin surface, and a calculating device for calculating a water transpiration amount and an overall mass transfer coefficient of water in the stratum corneum epidermidis based on properties of the carrier gas and the humidity.

22 Claims, 8 Drawing Sheets

MEASURED:  NORMAL VOLUNTEER (26-YEAR-OLD FEMALE) ☐
VOLUNTEER WITH LOW-BARRIER SKIN (26-YEAR-OLD FEMALE) ■

CALCULATED: ———
- - - - -

METHOD FOR EVALUATING SKIN HEALTH

BACKGROUND OF THE INVENTION

1. Field of the Invention

The present invention relates to a method for evaluating skin health and an apparatus used therefor.

2. Description of the Related Art

A living body always exchanges a substance and energy with an environment under which the living body exists and it has various functions of adjusting the transport amount or exchange amount of the substance or energy in accordance with an environmental change. Above all, a function of restraining transpiration of water from the skin surface, thereby protecting the living body from drying is called a barrier function and it is medically important. As an index of the barrier function, a water transpiration amount from the skin or a transepidermal water loss (TEWL) has been used widely. In the conventional method, investigation on. a response of the physical properties of the skin to the environment must be carried out while changing the environment in a laboratory. It is utterly unfeasible, because a large-scaled apparatus and much labor and time are required.

SUMMARY OF THE INVENTION

The present inventors paid attention to the fact that conventionally, investigation of the TEWL of the skin included only that of the stratum corneum epidermidis but living cells therebelow were not taken into consideration. According to the conventional way of thinking, an increase in TEWL owed to deterioration in the barrier function of the stratum corneum epidermidis. An increase in TEWL, however, is sometimes caused by abnormalities in the living cells below the normal stratum corneum epidermidis, and in such a case, correct diagnosis cannot be conducted.

The present inventors therefore classified the structure of the skin into the stratum corneum epidermidis and living cells therebelow and considered that TEWL might be influenced not only by the water permeability through the stratum corneum epidermidis but also by a difference (driving force) in the activity of water (or water vapor partial pressure) between the structure formed of living cells present below the stratum corneum epidermidis and the outside world. It is presumed that the activity of water in the living cells below the stratum corneum epidermidis reflects the concentration or composition of water and also bio-reaction so that it varies depending on the properties or disease of the skin, metabolism or even age. As described above, the present inventors have found that it is important, for appropriate skin care based on not only the working degree of a barrier function but also the properties or disease of the skin, metabolism or bio-reaction, to evaluate water permeability (overall mass transfer coefficient) through the stratum corneum epidermidis and water supplying capability (activity or water vapor partial pressure) in the living cells below the stratum corneum epidermidis separately from the water transpiration amount measured by using a specified apparatus. The present inventors have also found that the use of these evaluations in combination as an objective index of skin health makes it possible to conduct skin care in accordance with the skin health of each subject.

In one aspect of the present invention, there is thus provided a method for evaluating water permeability through the stratum corneum epidermidis based on a water transpiration amount, which comprises feeding, through a gas inlet, a carrier gas having certain properties to a skin surface to be measured; measuring, by a humidity sensor, the humidity of the carrier gas which has been discharged from a gas exhaust, passing over the skin surface to be measured; and calculating the water transpiration amount from the response of the sensor and calculating, by a predetermined analyzing method, an overall mass transfer coefficient of water in the stratum corneum epidermidis; and an apparatus used for the above-described method.

In another aspect of the present invention, there is also provided a method for evaluating, based on a water transpiration amount, water supplying capability of a structure which lies below the stratum corneum epidermidis and is formed of living cells, which comprises feeding, through a gas inlet, a carrier gas having certain properties to a skin surface to be measured; measuring, by a humidity sensor, the humidity of the carrier gas which has been discharged from a gas exhaust, passing over the skin surface to be measured; and calculating the water transpiration amount from the response of the sensor and calculating, by a predetermined analyzing method, a water vapor partial pressure of the structure which lies below the stratum corneum epidermidis and is formed of living cells; and an apparatus used for the above-described method.

In a further aspect of the present invention, there is also provided a method for evaluating skin health based on a water transpiration amount, which comprises feeding, through a gas inlet, a carrier gas having certain properties to a skin surface to be measured; measuring, by a humidity sensor, the humidity of the carrier gas which has been discharged from a gas exhaust, passing over the skin surface to be measured; and calculating the water transpiration amount based on the response of the sensor and calculating both an overall mass transfer coefficient of water in the stratum corneum epidermidis and a water vapor partial pressure of a structure which lies below the stratum corneum epidermidis and is formed of living cells by employing a predetermined analyzing method.

The terms "water permeability through the stratum corneum epidermidis", "overall mass transfer coefficient of the stratum corneum epidermidis", "water vapor partial pressure of a (the) structure which lies below the stratum corneum epidermidis and is formed of living cells" and "water supplying capability of a (the) structure which lies below the stratum corneum epidermidis and is formed of living cells" may be replaced with the simple terms "water permeability", "overall mass transfer coefficient", "water vapor partial pressure", and "water supplying capability", respectively.

According to the present invention, it is possible to evaluate water permeability and water supplying capability separately by analyzing the measured value of a water transpiration amount in different manners, and employ them as an index for a barrier function, skin conditions or disease, metabolism or bio-reaction. In addition, it is possible to use them in combination as an objective index of the skin health.

DETAILED DESCRIPTION OF THE PREFERRED EMBODIMENTS

The apparatus for evaluating water permeability and/or water supplying capability according to the present invention is equipped with (1) means for feeding, from a gas inlet, a carrier gas having certain properties to a skin surface to be measured, (2) means for measuring the humidity of the carrier gas, which has passed over the skin surface to be measured and has then been discharged from a gas exhaust, by a humidity sensor, and (3) means for calculating a water transpiration amount based on the response of the sensor, thereby calculating an overall mass transfer coefficient and/or water vapor partial pressure by a predetermined analyzing method.

Figure 1:
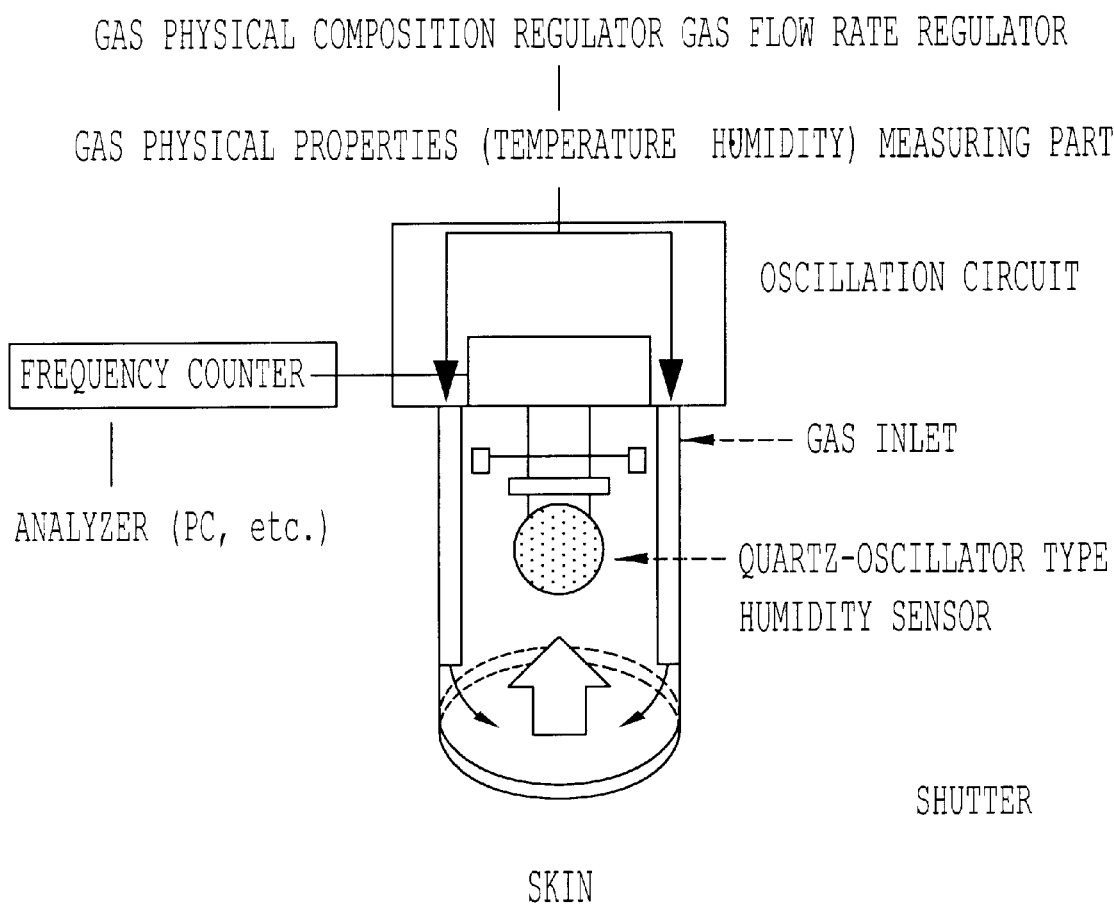
FIG. 1 is a schematic view illustrating a skin-health-evaluating apparatus according to the present invention.

The apparatus of the present invention is schematically illustrated in FIG. 1.

Described specifically, the apparatus is, for example, formed of a cylindrical body having inside thereof a humidity sensor, an opening at each of the top and bottom portion, a gas inlet on the side wall portion for feeding a gas having a fixed water content to a surface to be measured, and a freely openable or closable shutter portion at the bottom opening portion.

No particular limitation is imposed on the shape of the cylindrical body insofar as it has an opening portion at the top and bottom thereof. It may have a circular cylindrical shape, prismatic shape or the like. Concerning its size, a cylindrical body having a bottom opening area of about 0.2 to 10 cm$^2$ and a height of about 2 to 20 cm is preferred.

The gas inlet embedded in the side wall portion of the cylindrical body may be used insofar as it is capable of feeding a certain carrier gas to a skin surface to be measured. For example, the gas inlet may be formed by fixing a desired number of pipes each having a nozzle hole which opens downward and positioned slightly above the end of the bottom opening portion of the cylindrical body. For the carrier gas having certain properties, a gas having a predetermined temperature and humidity, for example, dry nitrogen and dry air, may be used.

It does not matter whether the shutter portion has any structure, for example, whether it has the opening/closing shutter mechanism of a camera or not, insofar as the bottom opening portion of the cylindrical body can be opened or closed as needed. A shutter having, at the lower part of the cylindrical body, a rotary slide plate disposed pivotally for opening or closing the bottom opening portion, or is made of a valve for opening or closing the bottom opening portion by the vertical movement is simple in structure and has excellent operability.

The temperature sensor is preferably disposed above the gas ejection port inside of the cylindrical body, which makes it possible to obtain a more stable and reliable measuring data. Any kind of a humidity sensor can be used, but use of a quartz oscillator humidity sensor is advantageous from the viewpoint of measuring accuracy.

Calculation of a water transpiration amount based on the response to the humidity sensor and then, calculation of an overall mass transfer coefficient and/or water vapor partial pressure through a predetermined analyzing method are conducted making use of an analyzer such as personal computer.

The water transpiration amount (J) is calculated as described below.

A water transpiration amount J (g/m$^2$·sec) from the skin can be expressed by the following equation:

$$J = \frac{1}{A} \frac{\Delta^H}{100} \rho^V$$

wherein, a change in relative humidity due to water transpiration from the skin which has been found from the response to a humidity sensor is $_A$H (%), a water content of the air having 100% RH at a given temperature is ρ (g/cm$^3$), a flow rate of a carrier gas is V (m$^3$/sec) and an area measured is A (m$^2$).

The overall mass transfer coefficient is calculated, in accordance with Fick's diffusion relation represented by the below-described Equation 1, from at least one parameter determined using at least one measuring result of a water transpiration amount obtained by measurement with variable micro-climates of the cell while changing the flow rate, water vapor partial pressure or temperature of a carrier gas. The greater the overall mass transfer coefficient, the higher water permeability through the stratum corneum epidermidis. The smaller the overall mass transfer coefficient, the lower water permeability through the stratum corneum epidermidis.

$$J = \frac{K_m D}{\delta}(C_d - C_r) \qquad \text{Equation 1}$$

wherein, $K_m$ is a partition coefficient, D represents a diffusion coefficient (m$^2$/sec), δ represents the thickness (m) of the stratum corneum epidermidis, and $C_d$ and $C_r$ represent the water concentrations (kg/m$^3$) of the water donor side and water receiver side, respectively.

More specifically, the overall mass transfer coefficient can be calculated using either one of the below-described analytical method (1) or (2).

(1) An overall mass transfer coefficient $k_p'$ (g/m$^2$·sec or g/m$^2$·sec·Pa) is determined by calculating the parameter K using the value of at least one water transpiration amount measured by changing the flow rate, water vapor partial pressure or temperature of a carrier gas and the value calculated in accordance with the below-described Equations 8 and 9, followed by calculation in accordance with the below-described Equation 2 using the resulting parameter K.

$$k_p' = dK\rho \frac{M_{H2O}}{M_{gas}} \qquad \text{Equation 2}$$

wherein, ρ represents the gas density (g/m$^3$), and M represents a molecular weight.

Such measurement with variable micro-climates of the cell can be conducted by changing any one of the flow rate, water vapor partial pressure and temperature of a carrier gas, of which the former two is preferred. In particular, measurement conducted changing both of the flow rate and water vapor partial pressure of a carrier gas is preferred, because it brings about highly-accurate evaluation results.

(2) The overall mass transfer coefficient is calculated in accordance with the below-described Equation 11 based on the measured values obtained by changing the water vapor pressure of at least two carrier gases.

Equations 2, 8, 9 and 11 are introduced from a model made as follows:

The atmosphere/skin system in which water transpiration is occurring is not a static system. Water transpiration from the skin is evidently a steady state and it is an irreversible process.

Figure 2:
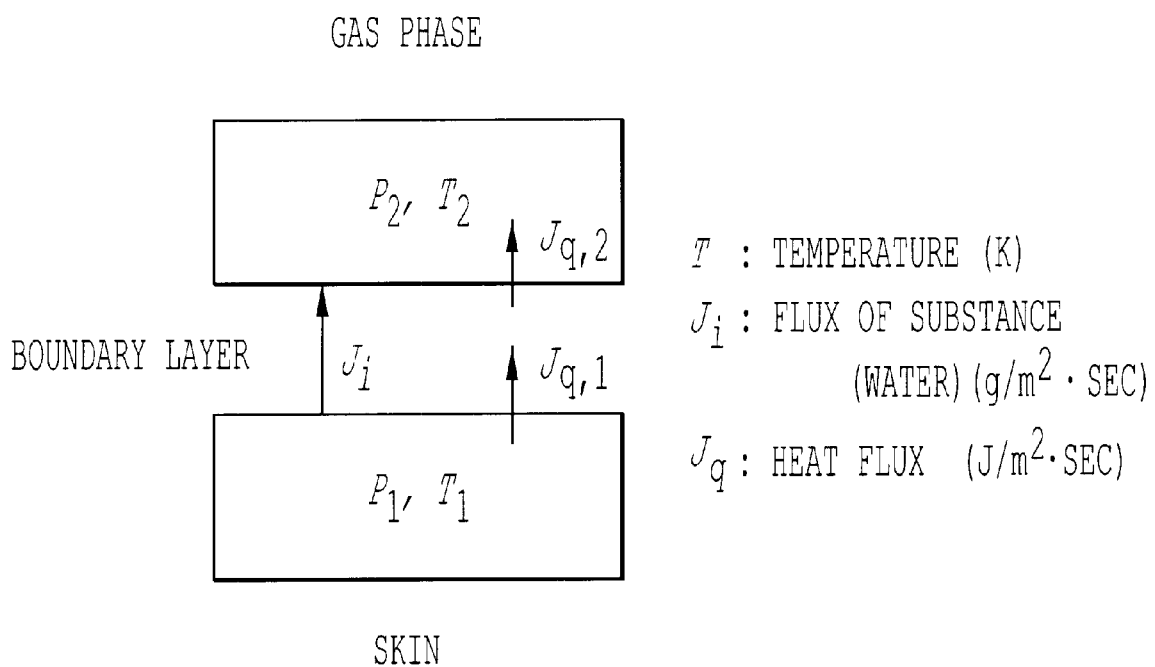
FIG. 2 illustrates the model of a mass and heat exchange between the atmosphere and the skin.

The atmosphere/skin system is supposed as an ideal system wherein heat and mass are transported through a thin layer (barrier layer) sandwiched between two pseudo-infinite phases having a predetermined temperature and composition (FIG. 2). The barrier layer is a layer highly resistant against the transfer of the mass and may exist on the side of the skin in this system. The bulk has uniform properties in each of the skin and gas phase and the changing rate of their properties are sufficiently low (so low that it can be regarded as changeless) relative to a time scale discussed here. The flux of each of heat and mass is strictly one-dimensional and vertical to the barrier layer and a gradient between two phases in temperature or chemical composition exists only on the barrier layer. The gas phase behaves as an ideal gas. For introduction of an analysis equation, a reversible path to the transportation of water from the skin to the atmosphere as described below is supposed.

$H_2O$ (skin, $P_1$, $T_1$)→$H_2O$ (liquid, $P_1$, $T_1$)→$H_2O$ (gas, $P_1$, $T_1$)→$H_2O$ (gas, $P_1$, $T_2$)→$H_2O$ (gas, $P_2$, $T_1$)

(A) Introduction of an Analysis Equation of the Transportation Rate and Direction of Water Which has Passed Through the Atmosphere/Skin Interface In accordance with the thermodynamic method based on an irreversible process, the below-described Equation 3 for analyzing the flux $J_i$ of water which has passed through the atmosphere/skin interface is introduced.

$$J_i = \frac{dP}{dt} = \frac{KP_m}{RT_m}\left(q^* T_2 - \frac{T_1}{T_m} + RT_m \ln\frac{kP^*}{P_2}\right) \quad \text{Equation 3}$$

wherein, q* represents a thermal change relating to isothermal transfer of a solute or vapor from the skin to the atmospheric layer, K stands for a rate constant (1/sec), k stands for a constant, $P^*$ stands for saturated vapor pressure, $P_m$ stands for a mean water vapor partial pressure within a barrier layer and $T_m$ stands for a mean temperature within a barrier layer.

Figure 3:
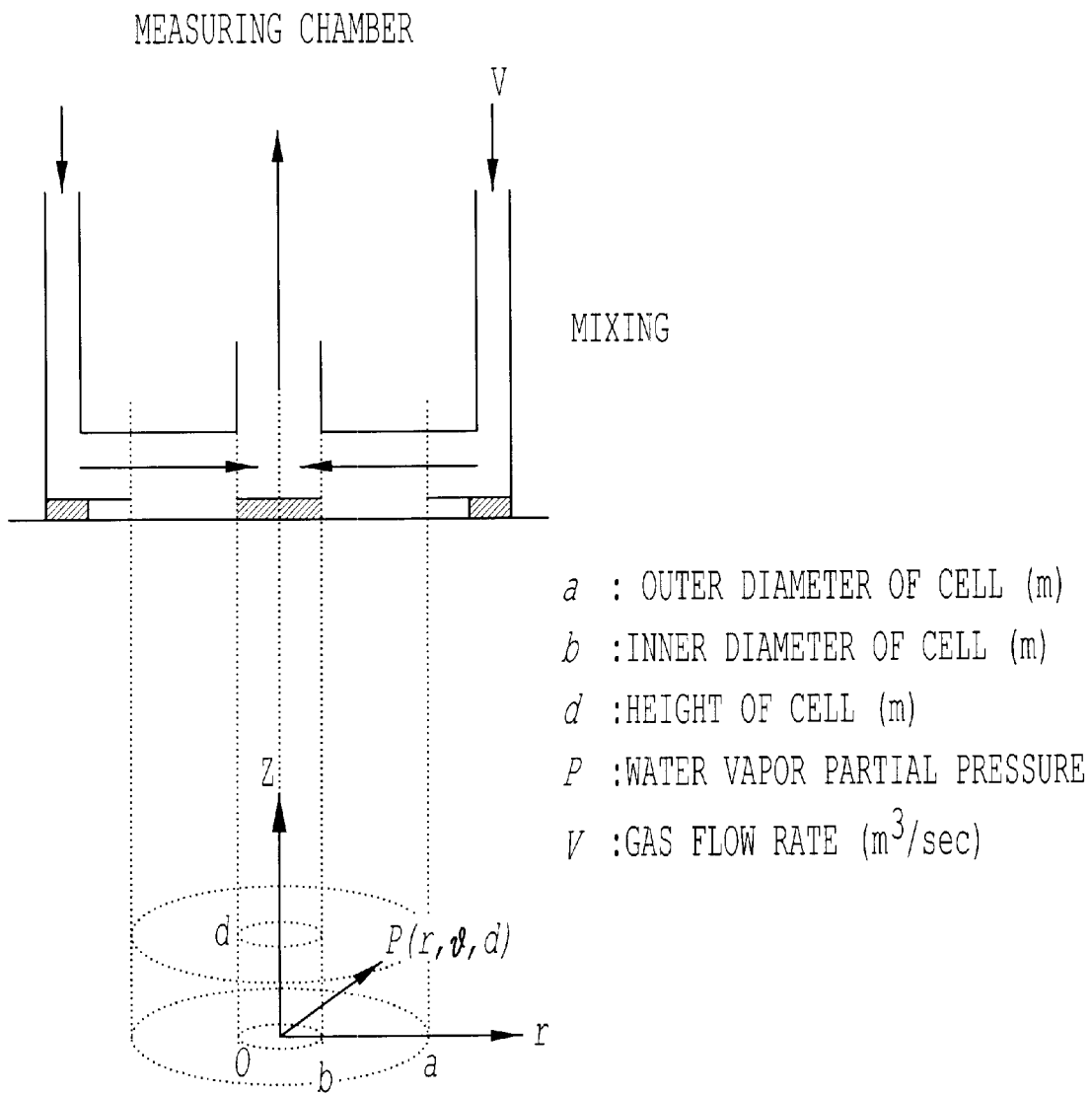
FIG. 3 is a cross-sectional view illustrating a measuring cell.
Figure 4:
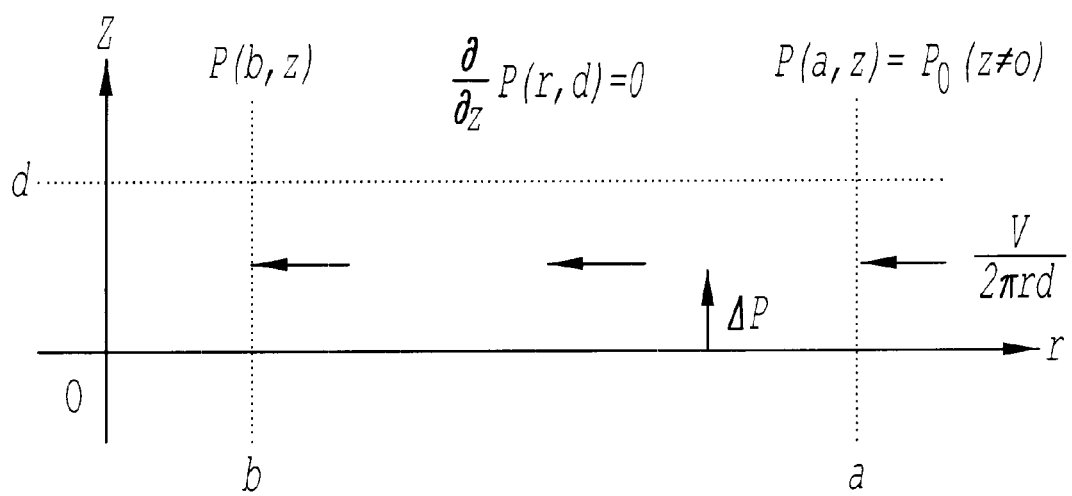
FIG. 4 is a schematic view illustrating the measuring part of a water transpiration amount (the upper portion illustrates the cross-section of the cylindrical body, while the lower portion illustrates the circular cylindrical coordinates)

(B) Introduction of an Analysis Equation of Water Vapor Pressure Distribution Inside of the Measuring Cell The shape of the cylindrical body which can be adopted here is not limited, but an analysis method will hereinafter be described using a cylindrical body which is formed to allow a carrier gas to flow along the outside wall, pass it over the surface of the skin and discharge it from the center of the cylinder. When it is assumed that the carrier gas flows along the outside wall of the cylindrical body into the inside of the cell at a flow rate of V (m³/sec), passes over the surface of the skin and is then discharged (FIGS. 3 and 4), the diffusion equation in this measuring system can be expressed as the following $$\frac{\partial P}{\partial t} = D\frac{1}{r}\frac{\partial}{\partial r}\left(r\frac{\partial P}{\partial r}\right) + \frac{V}{2\pi rd}\frac{\partial P}{\partial r} + D\frac{\partial^2 P}{\partial z^2} \quad \text{Equation 4}$$

wherein, D (m²/sec) stands for a diffusion coefficient of water into the atmospheric layer.

Under a steady state, Equation 4 is equal to 0, leading to the following Equation 5.

$$D\frac{1}{r}\frac{\partial}{\partial r}\left(r\frac{\partial P}{\partial r}\right) + \frac{V}{2\pi rd}\frac{\partial P}{\partial r} + D\frac{\partial^2 P}{\partial z^2} = 0 \quad \text{Equation 5}$$

When Equation 5 is solved under the following boundary conditions:

$$\begin{cases} P(a, z) = P_0 (z \neq 0) \\ \frac{\partial}{\partial z}P(r, d) = 0 \end{cases}$$

wherein, $P_0$ stands for a water vapor partial pressure in the gas before the gas enters into the cell, the solution of Equation 5 is equal to Equation 6 when water vapor is generated continuously at r=a to b.

$$P(b, z) = P_0 + \int_a^b \frac{dP_1}{ds}\left[1 + 2\sum_{m=1}^{\infty}\cos\left(\frac{m\pi z}{d}\right)\right]\frac{\sum_{n=1}^{even} a_n b^n}{\sum_{n=1}^{even} a_n s^n}ds \quad \text{Equation 6}$$

$$a_0 = 1$$

$$a_n = \frac{m^2\pi^2}{d^2 n\left(n + \frac{V}{2\pi Dd}\right)}a_{n-2} \quad (n \geq 2)$$

(C) Introduction of an Analysis Equation for the Measurement with Variable Micro-climates of the Cell The following Equation 8:

$$P(b, z) = P_0 + \int_a^b \frac{dP}{ds}\left[1 + 2\sum_{m=1}^{\infty}\cos\left(\frac{m\pi z}{d}\right)\right]\frac{\sum_{n=1}^{even} a_n b^n}{\sum_{n=1}^{even} a_n s^n}ds \quad \text{Equation 8}$$

$$= P_0 + \int_b^a \frac{2\pi sd}{V}\frac{KP_m}{RT_m}\left[q^*T_2 - \frac{T_1}{T_m} + RT_m\ln\frac{kP^*}{P(s,0)}\right]\left[1 + 2\sum_{m=1}^{\infty}\cos\left(\frac{m\pi z}{d}\right)\right]\frac{\sum_{n=0}^{even} a_n b^n}{\sum_{n=0}^{even} a_n s^n}ds$$

$$a_0 = 1$$

$$a_n = \frac{m^2\pi^2}{d^2 n\left(n + \frac{V}{2\pi Dd}\right)}a_{n-2} \quad (n \geq 2)$$

that is, an equation for analyzing a relation between measuring conditions and a water transpiration amount is introduced by uniting the following Equation 7:

$$-\frac{dP}{dr} = \frac{\frac{dP}{dt}}{\frac{dr}{dt}} = \frac{2\pi rd}{V}\frac{KP_m}{RT_m}\left(q^*T_2 - \frac{T_1}{T_m} + RT_m\ln\frac{kP^*}{P_2}\right) \quad \text{Equation 7}$$

available from Equation 3 for analyzing the transpiration rate of water which has passed through an atmosphere/skin interface and Equation 5 for analyzing the water vapor partial pressure distribution inside of the measuring cell.

With regards to the second member on the right side of Equation 8, the contribution of this member due to a temperature difference is within 4%, negligible small when a temperature difference (about 30K at the maximum) between the ordinary environment and inside of the living body is taken into consideration, which makes it possible to introduce the following Equation 8-2:

$$P(b, z) = P_0 + \int_b^a \frac{2\pi s d}{V} K P_m \ln \frac{kP^*}{P(s, 0)} \quad \text{Equation 8-2}$$

$$\left[ 1 + 2 \sum_{m=1}^{\infty} \cos\left(\frac{m\pi z}{d}\right) \right] \frac{\sum_{n=1}^{even} a_n b^n}{\sum_{n=1}^{even} a_n s^n} ds$$

Here, with a system which satisfies $_\Delta P \ll P_m$ (which is assumed to correspond to the atmosphere/skin system), approximation represented by $\ln(P_1/P_2) \cong _\Delta P/P_m$ is conducted, whereby the following Equation 8-3 is introduced:

$$P(b, z) = P_0 + \int_b^a \frac{2\pi s d}{V} \quad \text{Equation 8-3}$$

$$K[kP^* - P(s, 0)] \left[ 1 + 2 \sum_{m=1}^{\infty} \cos\left(\frac{m\pi z}{d}\right) \right] \frac{\sum_{n=0}^{even} a_n b^n}{\sum_{n=0}^{even} a_n s^n} ds$$

For analysis of measurements with variable microclimates of the cell, Equation 8-2 or 8-3 may be used instead of Equation 8.

(D) Introduction of Water Permeability

A water transpiration amount (g/m$^2$·sec) under desired measuring conditions is calculated in accordance with the following Equation 9.

$$J = \frac{\left(\int_0^d P(b, z) dz - P_0\right) \rho V}{\pi(a^2 - b^2)} \frac{M_{H_2O}}{M_{gas}} \quad \text{Equation 9}$$

wherein, $\rho$ stands for a gas density (g/m$^3$) and M stands for molecular weight.

When a water vapor partial pressure inside of the measuring cell increases by $_\Delta P$ per unit time owing to water vapor transpiration from the skin surface, the following Equation 10:

$$J = \frac{1}{A} \rho A d \frac{dP}{dt} \quad \text{Equation 10}$$

$$J = \frac{1}{\pi(a^2 - b^2)} \rho \frac{M_{H_2O}}{M_{gas}} \pi(a^2 - b^2) d \frac{KP_m}{RT_m} \left[ q^* T_1 - \frac{T_2}{T_m} + RT_m \ln \frac{kP^*}{P_2} \right]$$

can be introduced.

This Equation 10 is separated into restraining and driving force terms. The contribution caused by a difference between a temperature under the ordinary circumstance and that inside of the living body is within 4% and its influence is negligible. With a system which satisfies $_\Delta P \ll P_m$ (which is assumed to correspond to the atmosphere/skin system), approximation represented by $\ln(P_1/P_2) \cong _\Delta P/P_m$ is conducted, leading to the following Equation 11:

$$J = \frac{1}{\pi(a^2 - b^2)} \rho \frac{M_{H_2O}}{M_{gas}} \pi(a^2 - b^2) d \frac{KP_m}{RT_m} \left[ q^* T_1 - \frac{T_2}{T_m} + RT_m \ln \frac{kP^*}{P_2} \right] \quad \text{Equation 11}$$

$$\cong dK\rho \frac{M_{H_2O}}{M_{gas}} \times (kP^* - P_1)$$

and an overall mass transfer coefficient (g/m$^2$·sec or g/m$^2$·sec·Pa), which means water permeability, can be determined from the following Equation 2:

$$k'_p = dK\rho \frac{M_{H_2O}}{M_{gas}} \quad \text{Equation 2}$$

The "overall mass transfer coefficient" introduced from the measuring results of a water transpiration amount is also called mass transfer coefficient, permeability coefficient, permeation or permeability. The diffusion coefficient or diffusion properties determined from the overall mass transfer coefficient, for example, in accordance with the below-described relationship can also be used for the evaluation of water permeability.

$$k_p' = K_m \cdot D/\delta$$

wherein, $k_p'$ stands for an overall mass transfer coefficient, $K_m$ stands for a partition coefficient, D stands for a diffusion coefficient and $\delta$ stands for the thickness of a membrane.

Each of the terms "water permeation", "barrier function", "barrier characteristics", "barrier properties", "barrier capacity" and "water loss suppressing power" has the same meaning as the term "water permeability" through the stratum corneum epidermidis evaluated using an overall mass transfer coefficient introduced from the measuring results of a water transpiration amount and they can be used similarly.

(E) Introduction of Water Supplying Capability

The term "water supplying capability" as used herein means a water vapor partial pressure in a structure which lies below the stratum corneum epidermidis and is formed of living cells. The water supplying capability corresponds to kP· in Equation 3 which is available as a result of analysis of measurement with variable micro-climates of the cell using Equation 8, 8-2 or 8-3. According to Equation 11, when the activity of water (water vapor partial pressure) contained in a gas phase or a carrier gas is equal to that of a structure which lies below the stratum corneum epidermidis and is formed of living cells, a water transpiration amount (J) should become 0. It is therefore possible to apply Equation 11 to a change of a water transpiration amount due to a water vapor partial pressure of a gas phase or a carrier gas, thereby determining, as the value of the intercept x, a water vapor partial pressure, that is, water supplying capability, in a structure which lies below the stratum corneum epidermidis and is formed of living cells.

The "water vapor partial pressure" introduced from the measuring results of a water transpiration amount is also called "water vapor pressure", "vapor pressure of water" or "fugacity" and "water content", "concentration of water", "activity" or "water vapor amount" determined from the water vapor partial pressure can also be used for the evaluation of water supplying capability. The concentration of water can be found, for example, by the following relationship:

$$P = H \cdot C$$

wherein, P stands for a water vapor partial pressure, H represents a constant and C represents the concentration of water.

Each of the terms "power for promoting water transpiration", "water content", "activity", "moisturized feeling" and "concentration of water" has the same meaning as the term "water supplying capability" introduced from the measuring results of a water transpiration amount and they can be used similarly.

As described above, "water permeability" evaluated in the present invention represents the function of the stratum corneum, while "water supplying capability" represents the function of a structure which lies below the stratum corneum epidermidis and is formed of living cells. The skin health (including the stratum corneum and living cells therebelow) can be evaluated totally by the evaluation of these two factors.

For example, when no change is observed from the living cells below the stratum corneum and an abnormality exists only in the stratum corneum, only water permeability shows an abnormal value. When not the stratum corneum but the living cells therebelow are abnormal, on the other hand, only water supplying capability becomes abnormal. It is of course possible to diagnose the case where both are abnormal.

EXAMPLES

Example 1

Evaluation results of the water permeability and water supplying capability of a normal volunteer (26-year-old female) and a volunteer (26-year-old female) with low-barrier-skin at their cheek portion will next be described.

(1) Evaluation Method 1

Figure 5B:
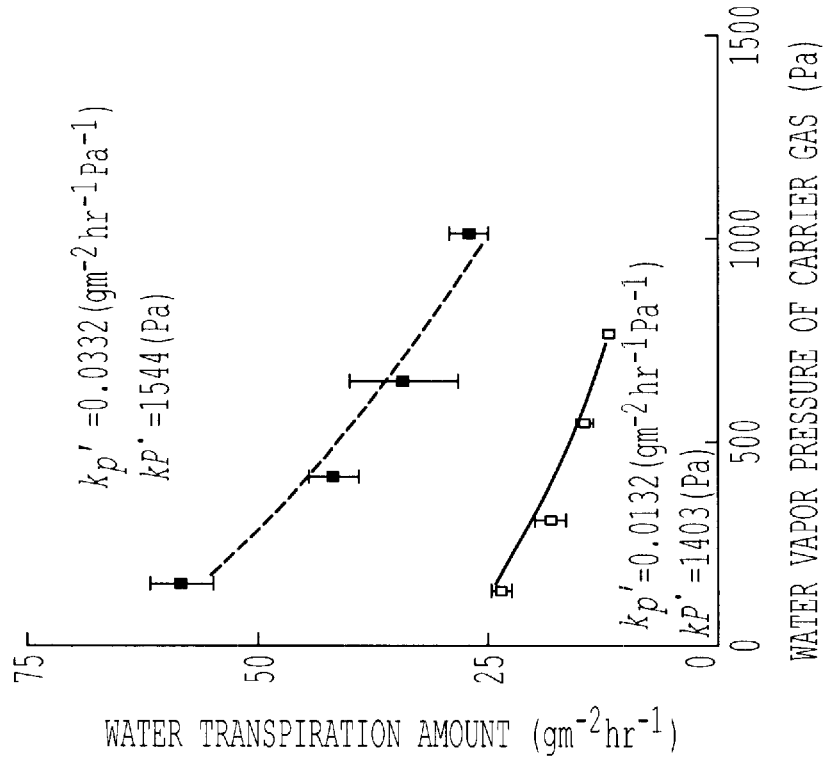
FIG. 5 illustrates water permeability and water supplying capability as measured at varied flow rates and water vapor partial pressures of a carrier gas.
Figure 5A:
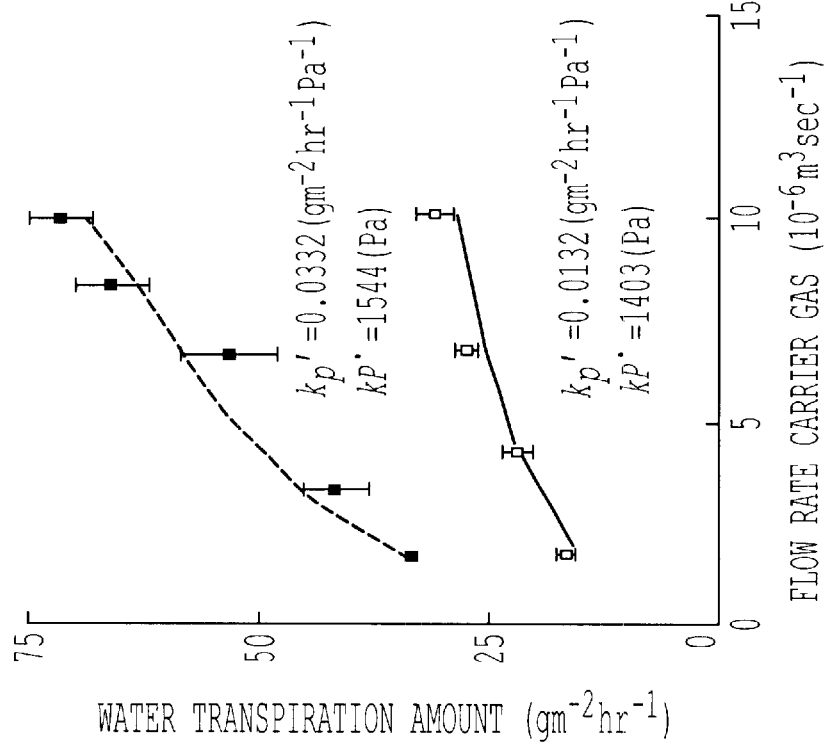

In FIG. 5, illustrated are overall mass transfer coefficient $k_p'$ (that is, water permeability) and water vapor partial pressure $kP^*$ (that is, water supplying capability) calculated from K,k determined by fitting the values measured by changing the flow rate and water vapor pressure of a carrier gas and the values calculated according to Equations 8 and 9. The water permeabilities of the normal volunteer and volunteer with low-barrier-skin were 0.0132 and 0.0332 (gm$^{-2}$hr$^{-1}$Pa$^{-1}$), respectively. Their water supplying capabilities were 1544 and 1403 (Pa), respectively.

(2) Evaluation Method 2

Figure 6:
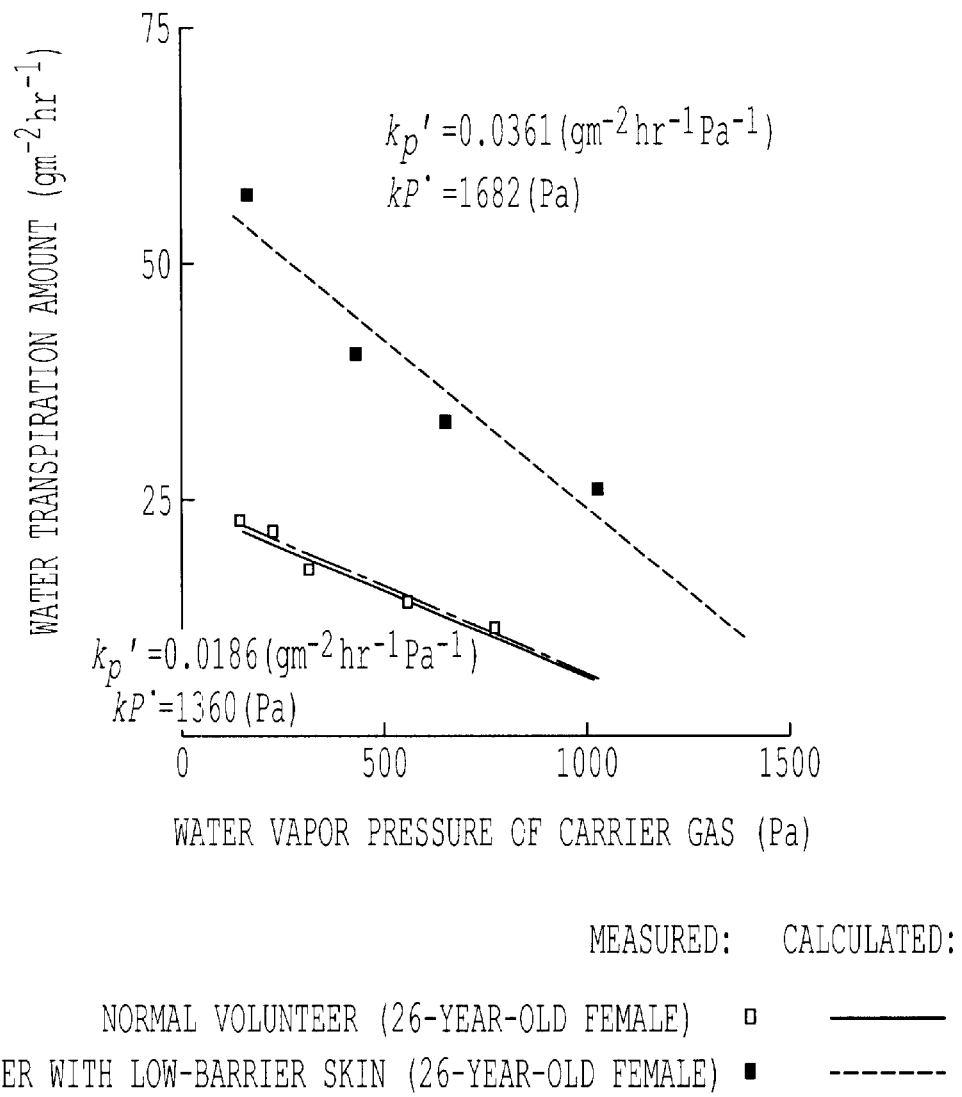
FIG. 6 illustrates water permeability and water supplying capability as measured only at varied water vapor partial pressures of a carrier gas.

In FIG. 6, illustrated are water permeability and water supplying capability calculated based on Equation 11 from the value measured by changing the water vapor partial pressure of a carrier gas. The water permeabilities of the normal volunteer and volunteer with low-barrier-skin were 0.0186 and 0.0361 (gm$^{-2}$hr$^{-1}$Pa$^{-1}$), respectively. Their water supplying capabilities were 1360 and 1682 (Pa), respectively.

Comparison between FIG. 5 and FIG. 6 indicates that the accuracy of the former evaluation method is high, however, the latter one which is inferior in accuracy to the former one can also be employed as a method for evaluation of both of water permeability and water supplying capability.

Example 2

Evaluation results of the water permeability and water supplying capability of Volunteer A (36-year-old female with normal skin) and Volunteer B (32-year-old female with atopic skin) at their cheek portion will next be described.

Figure 7:
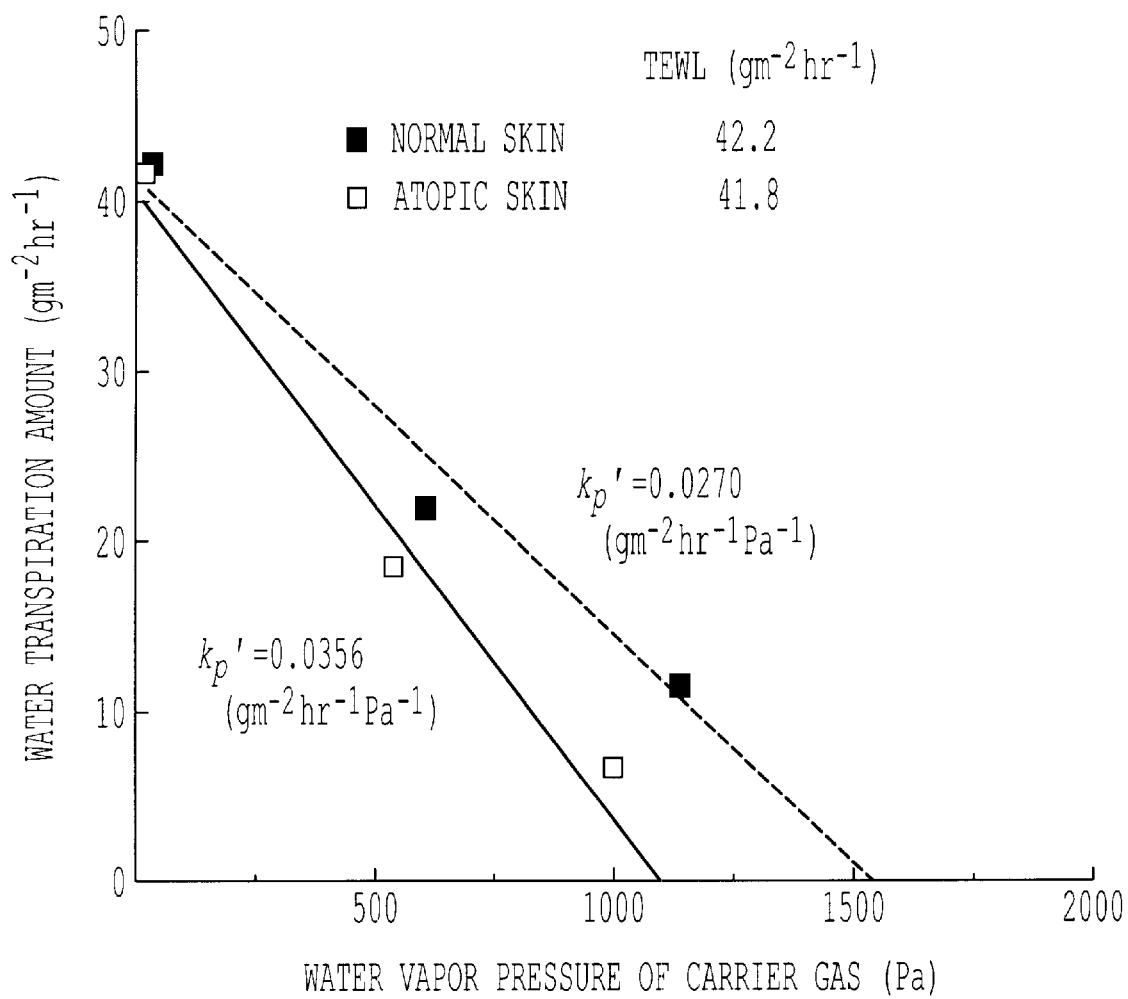
FIG. 7 illustrates variations in a water transpiration amount from each of the healthy skin and atopic skin due to a change in water vapor partial pressure of a carrier gas.

Water permeability calculated, in accordance with Equation 11, from the values measured at varied water vapor partial pressures of a carrier gas is illustrated in FIG. 7. The TEWL (extrapolated value when the humidity of a carrier gas is 0% RH) and water permeability of Volunteer A and Volunteer B were 41.4 and 40.9 (gm$^{-2}$hr), and 0.0270 and 0.0356 (gm$^{-2}$hr$^{-1}$Pa$^{-1}$), respectively, suggesting that the water permeability of Volunteer B was greater than that of Volunteer A in spite that they were almost similar in TEWL. According to the conventional evaluation based on the value of TEWL, they were regarded to have an equal barrier function. When water permeability is employed as an index, on the other hand, the barrier function can be evaluated more precisely, reflecting the actual skin state.

Example 3

Evaluation results of water permeability and water supplying capability of a normal volunteer (31-year-old female) at her cheek portion with the passage of time, more specifically, after 0, 2 and 4 weeks, will next be described.

Figure 8:
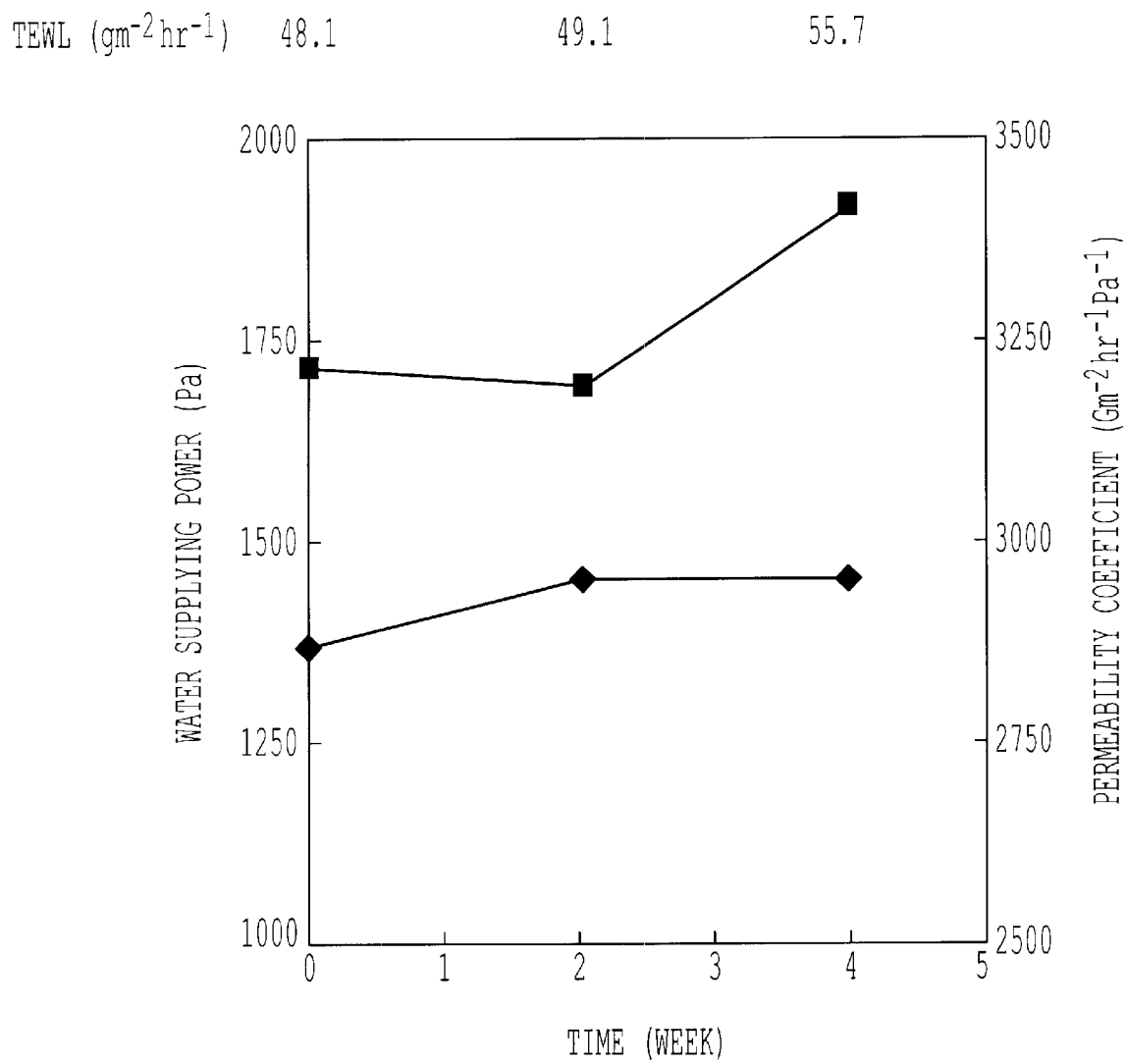
FIG. 8 illustrates variations of water permeability and water supplying capability with the passage of time.

Changes in each of water permeability and water supplying capability after 0, 2 and 4 weeks which were calculated, in accordance with Equation 11, from the values measured at varied water vapor partial pressures of a carrier gas are shown in FIG. 8. The TEWLs after 0, 2 and 4 weeks were 48.1, 49.1 and 55.7 (gm$^{-2}$hr$^{-1}$), respectively. FIG. 8 indicates that the water permeability showed almost no change from 0 to 4 weeks, while the water supplying capability showed a drastic increase at the fourth week. As a result of diagnosis by a doctor, the skin condition was substantially the same for those four weeks, while as a result of questionnaire, the physical condition of the volunteer was bad owing to the worsening of pollinosis from the second week to the fourth week. Although it was conventionally impossible to measure a change in the physical condition, at least a change in the physical condition by pollinosis was grasped by using the water supplying capability as an evaluation index.

What is claimed is:

1. An apparatus for evaluating water permeability of the stratum corneum epidermidis, said apparatus comprising:

feeding means for feeding a carrier gas to a skin surface to be measured;

measuring means for measuring humidity of the carrier gas discharged from the feeding means over the skin surface; and calculating means for calculating a water transpiration amount and an overall mass transfer coefficient of water in the stratum corneum epidermidis based on properties of the carrier gas and the measured humidity.

2. The apparatus of claim 1, wherein:

the carrier gas comprises one of a dry nitrogen gas and a dry air; and the properties of the carrier gas comprises predetermined temperature and predetermined water vapor partial pressure.

3. An apparatus for evaluating water supplying capability of cells below stratum corneum epidermidis said apparatus comprising:

feeding means for feeding a carrier gas to a skin surface to be measured;

measuring means for measuring humidity of the carrier gas discharged from the feeding means over the skin surface; and calculating means for calculating a water transpiration amount and a water vapor partial pressure of the cells below the stratum corneum epidermidis based on properties of the carrier gas and the measured humidity.

4. The apparatus of claim 3, wherein:

the carrier gas comprises one of a dry nitrogen gas and a dry air; and the properties of the carrier gas comprises predetermined temperature and predetermined water vapor partial pressure.

5. A method for evaluating skin health, comprising the steps of:

feeding a carrier gas to a skin surface to be measured;

measuring humidity of the carrier gas discharged over the skin surface; and calculating a water transpiration amount, an overall mass transfer coefficient of water in the stratum corneum epidermidis, and water vapor partial pressure of the cells below the stratum corneum epidermidis based on properties of the carrier gas and the measured humidity.

6. The apparatus of claim 5, wherein:

the carrier gas comprises one of a dry nitrogen gas and a dry air; and the properties of the carrier gas comprises predetermined temperature and predetermined water vapor partial pressure.

7. A method for evaluating water permeability of stratum corneum epidermidis, comprising the steps of:

feeding a carrier gas to a skin surface to be measured;

measuring humidity of the carrier gas discharged over the skin surface; and calculating a water transpiration amount and an overall mass transfer coefficient of water in the stratum corneum epidermidis based on properties of the carrier gas and the measured humidity.

8. The method of claim 7, wherein:

the carrier gas comprises one of a dry nitrogen gas and a dry air; and the properties of the carrier gas comprises predetermined temperature and predetermined water vapor partial pressure.

9. A method for evaluating water supplying capability of cells below stratum corneum epidermidis, said method comprising the steps of:

feeding a carrier gas to a skin surface to be measured;

measuring humidity of the carrier gas discharged over the skin surface; and calculating a water transpiration amount and a water vapor partial pressure of the cells below the stratum corneum epidermidis based on properties of the carrier gas and the measured humidity.

10. The method of claim 9, wherein:

the carrier gas comprises one of a dry nitrogen gas and a dry air; and the properties of the carrier gas comprises predetermined temperature and predetermined water vapor partial pressure.

11. An apparatus for evaluating water permeability of the stratum corneum epidermidis, said apparatus comprising.

a gas inlet configured to feed a carrier gas to a skin surface to be measured;

a humidity sensor positioned to measure humidity of the carrier gas discharged from the gas inlet over the skin surface; and an analyzer configured to calculate a water transpiration amount and an overall mass transfer coefficient of water in the stratum corneum epidermidis based on properties of the carrier gas and the measured humidity.

12. The apparatus of claim 11, further comprising a body configured to enclose the skin surface to be measured.

13. The apparatus of claim 11, wherein:

the carrier gas comprises one of a dry nitrogen gas and a dry air; and the properties of the carrier gas comprises predetermined temperature and predetermined water vapor partial pressure.

14. The apparatus of claim 11, further comprising:

a gas composition regulator configured to regulate a gas composition of the carrier gas to the gas inlet;

a gas flow rate regulator configured to regulate a flow rate of the carrier gas to the gas inlet; and a measuring device configured to measure the properties of the carrier gas before discharging from the gas inlet.

15. The apparatus of claim 11, wherein the humidity sensor comprises a quartz-oscillator humidity sensor.

16. The apparatus of claim 11, wherein the analyzer comprises a personal computer connected to a frequency counter and an oscillation circuit.

17. An apparatus for evaluating water supplying capability of cells below stratum corneum epidermidis said apparatus comprising:

a gas inlet configured to feed a carrier gas to a skin surface to be measured;

a humidity sensor positioned to measure humidity of the carrier gas discharged from the gas inlet over the skin surface; and an analyzer configured to calculate a water transpiration amount and a water vapor partial pressure of the cells below the stratum corneum epidermidis based on properties of the carrier gas and the measured humidity.

18. The apparatus of claim 17, further comprising a body configured to enclose the skin surface to be measured.

19. The apparatus of claim 17, wherein:

the carrier gas comprises one of a dry nitrogen gas and a dry air; and the properties of the carrier gas comprises predetermined temperature and predetermined water vapor partial pressure.

20. The apparatus of claim 17, further comprising:

a gas composition regulator configured to regulate a gas composition of the carrier gas to the gas inlet;

a gas flow rate regulator configured to regulate a flow rate of the carrier gas to the gas inlet; and a measuring device configured to measure the properties of the carrier gas before discharging from the gas inlet.

21. The apparatus of claim 17, wherein the humidity sensor comprises a quartz-oscillator humidity sensor.

22. The apparatus of claim 17, wherein the analyzer comprises a personal computer connected to a frequency counter and an oscillation circuit.

* * * * *

UNITED STATES PATENT AND TRADEMARK OFFICE
CERTIFICATE OF CORRECTION

PATENT NO. : 6,533,725 B1
DATED : March 18, 2003
INVENTOR(S) : Koji Endo et al.

It is certified that error appears in the above-identified patent and that said Letters Patent is hereby corrected as shown below:

Column 11,
Line 20, delete "apparatus" and insert -- method --.

Signed and Sealed this

Twenty-sixth Day of August, 2003

JAMES E. ROGAN
*Director of the United States Patent and Trademark Office*